United States Patent
Anandan et al.

(10) Patent No.: US 9,478,809 B2
(45) Date of Patent: Oct. 25, 2016

(54) FLEXIBLE COMPOSITE SOLID POLYMER ELECTROCHEMICAL MEMBRANE

(71) Applicant: Ford Global Technologies, LLC, Dearborn, MI (US)

(72) Inventors: Venkataramani Anandan, Farmington Hills, MI (US); Andrew Robert Drews, Ann Arbor, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 559 days.

(21) Appl. No.: 13/943,082

(22) Filed: Jul. 16, 2013

(65) Prior Publication Data
US 2015/0024256 A1    Jan. 22, 2015

(51) Int. Cl.
| | |
|---|---|
| *H01M 6/12* | (2006.01) |
| *H01M 6/18* | (2006.01) |
| *H01M 10/056* | (2010.01) |
| *H01M 10/052* | (2010.01) |
| *H01M 8/10* | (2016.01) |
| *H01M 12/08* | (2006.01) |
| *G01N 27/333* | (2006.01) |

(52) U.S. Cl.
CPC ......... *H01M 6/187* (2013.01); *H01M 8/1041* (2013.01); *H01M 8/1065* (2013.01); *H01M 10/052* (2013.01); *H01M 10/056* (2013.01); *G01N 27/333* (2013.01); *H01M 8/1011* (2013.01); *H01M 12/08* (2013.01); *H01M 2008/1095* (2013.01); *H01M 2300/0065* (2013.01); *Y02E 60/50* (2013.01)

(58) Field of Classification Search
CPC .... H01M 6/187; H01M 10/056; Y02E 60/50
USPC .................................. 429/162, 306
See application file for complete search history.

(56) References Cited

U.S. PATENT DOCUMENTS

| | | | |
|---|---|---|---|
| 5,273,837 A | 12/1993 | Aitken et al. | |
| 6,623,881 B2 | 9/2003 | Badding et al. | |
| 6,660,419 B1 | 12/2003 | Nishida et al. | |
| 7,550,216 B2 | 6/2009 | Ofer et al. | |
| 7,736,772 B2 | 6/2010 | Sarkar et al. | |
| 2007/0238005 A1* | 10/2007 | Yagi ........................ B32B 15/08 429/509 |

OTHER PUBLICATIONS

Knauth, "Inorganic solid Li ion conductors: An overview", Solid State Ionics, 180, 2009, pp. 911-916.
Takada, "Progress and prospective of solid-state lithium batteries", SciVerse ScienceDirect, Acta Materialia, 61, 2013, pp. 759-770.
Yang et al., "Membranes in Lithium Ion Batteries", Membranes, 2, 2012, pp. 367-383.
Quartarone et al., "Electrolytes for solid-state lithium rechargeable batteries: recent advances and perspectives", Chem. Soc. Rev., 2011, 40, pp. 2525-2540.

* cited by examiner

*Primary Examiner* — Gary Harris
(74) *Attorney, Agent, or Firm* — Brooks Kushman P.C.; Damian Porcari

(57) ABSTRACT

A solid state battery includes a flexible polymer sheet, and an array of solid state pillars supported by and extending through the sheet. Each of the pillars has an anode layer, a cathode layer adjacent, and an inorganic solid electrolyte (ISE) layer interposed between the anode and cathode layers. A flexible electrochemical membrane includes a flexible polymer sheet, and an array of inorganic solid electrolyte pillars supported by the polymer sheet with each of the pillars extending through a thickness of the sheet to form an ionically conductive pathway therethrough.

14 Claims, 3 Drawing Sheets

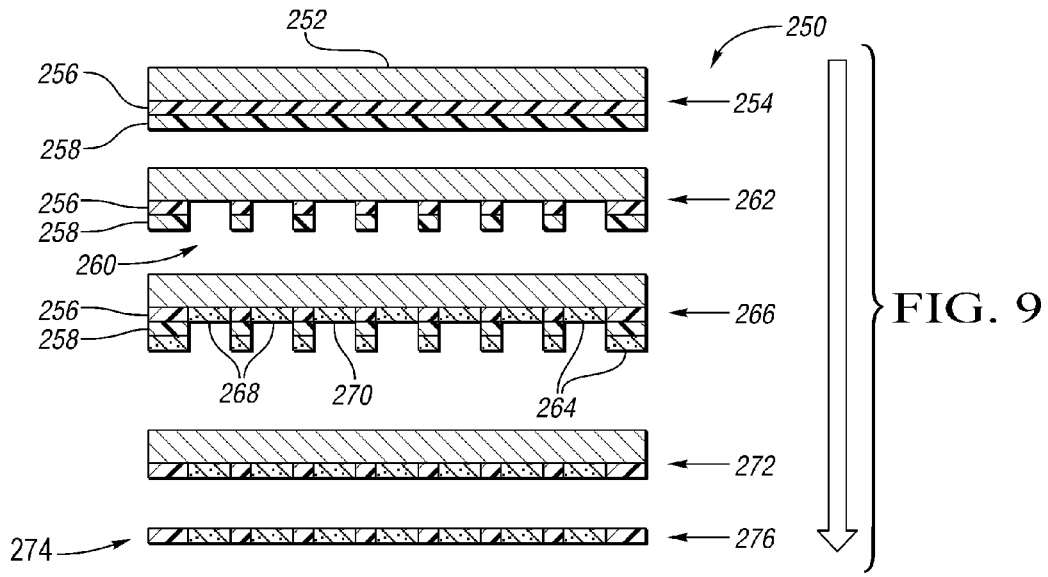
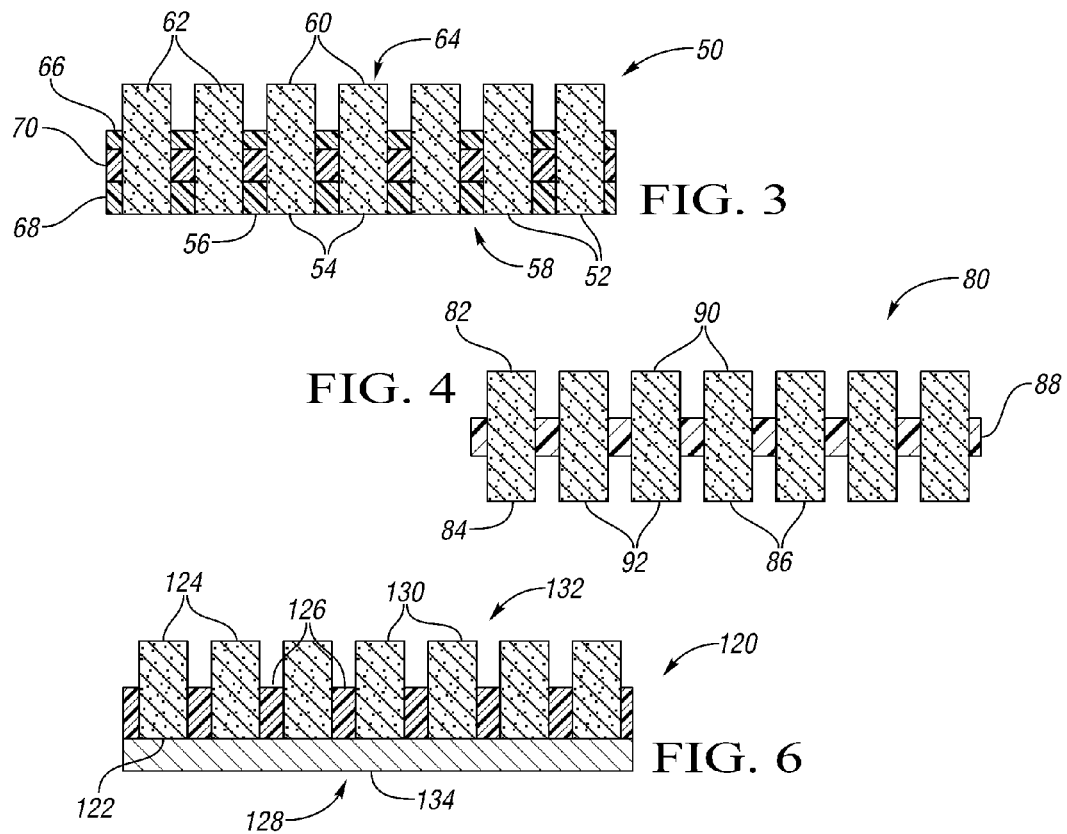

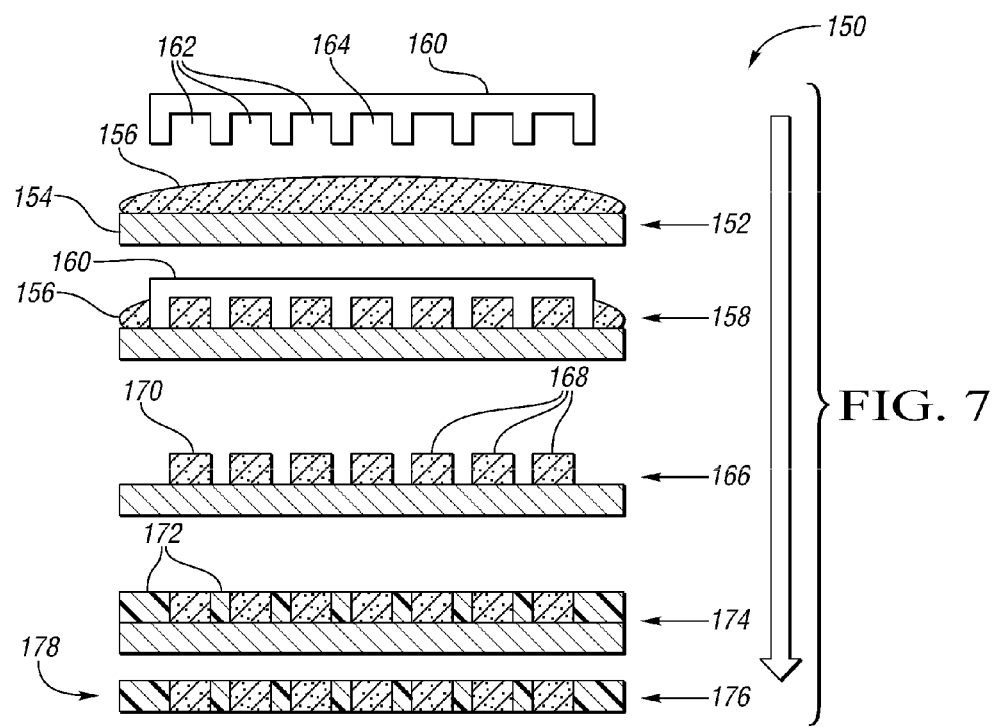
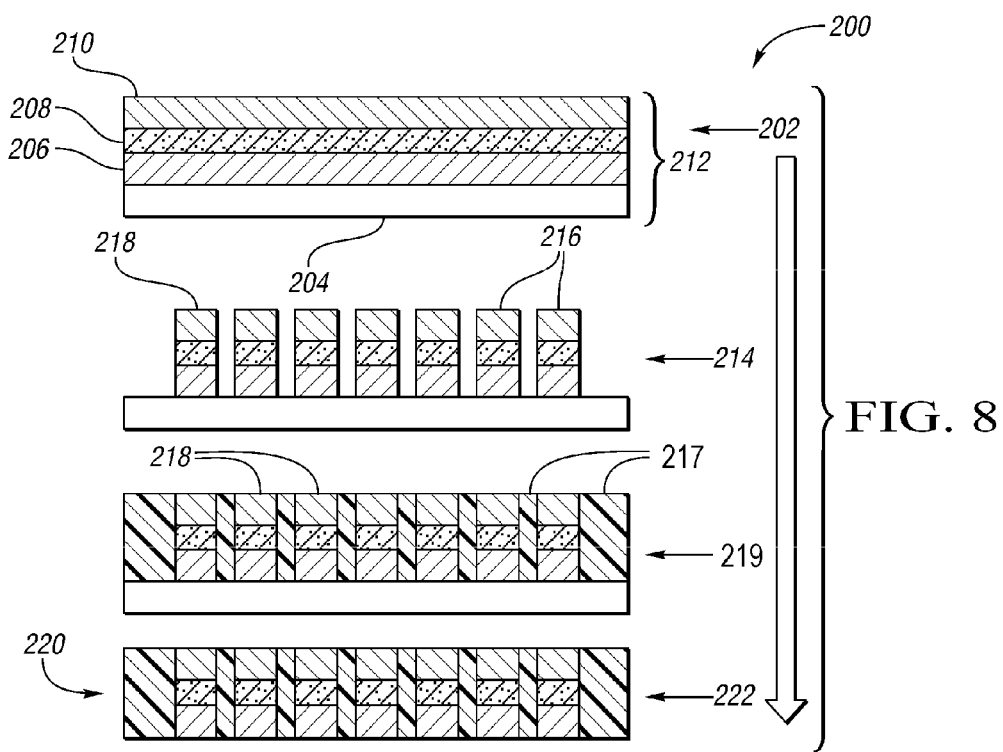

FLEXIBLE COMPOSITE SOLID POLYMER ELECTROCHEMICAL MEMBRANE

TECHNICAL FIELD

Various embodiments relate to a flexible composite electrochemical membrane or solid state battery and methods of making thereof.

BACKGROUND

An electrochemical membrane is a semipermeable or permeable membrane that provides ionic transport across the membrane. The ionic transport may be through diffusion, migration or convection, and occurs in response to a difference in chemical concentrations across the membrane or electrical polarization in devices such as a battery separator, a fuel cell membrane, a flow cell membrane, and the like. An electrochemical membrane may be used as an ion exchange device, for example, in a water softener system. Electrochemical membranes may also be used as ion selective membranes, for example, in a sensor such as a fluorine ion sensor.

Batteries, such as lithium ion batteries, conventionally contain a liquid electrolyte, such as an organic carbonate-based electrolyte, used in conjunction with a porous polymer membrane. Organic liquid electrolytes have a disadvantageous property that they may present a risk of a thermal event if not properly handled. Safer alternatives to a liquid electrolyte include a non-porous solid or polymer electrolyte. A polymer electrolyte has flexibility, but typically has an ionic conductivity that is too low for use in electrochemical applications. A solid electrolyte, which includes an inorganic solid electrolyte (ISE) material, has a sufficiently high ionic conductivity for use in electrochemical applications, but is rigid or inflexible. Various ISEs demonstrate comparable ionic conductivity to current liquid electrolytes, have resistance to thermal events, and are structurally rigid or inflexible which prevents penetration and possible short circuiting from Li metal dendrite growth. The benefits of an ISE are typically realized only in a purely solid state battery (SSB) where the ISE is a dense, sintered plate, and the plates are layered or stacked within the battery. Volume production of this battery configuration is difficult, for example, for an automotive battery. Another limitation to an ISE battery is that any active material must be in close physical contact with the ISE to allow for ionic transfer. For a dense sintered ISE plate, this may limit their application to thin layers of active material deposited directly onto the surface of the electrolyte. For these reasons, inorganic solid electrolytes are presently only being used in thin film batteries, where cathode, solid electrolyte and anode are deposited layer by layer by vapor deposition techniques such as sputtering.

A battery having a flexible membrane allows for high volume production that can be incorporated into a wound cell, e.g. spiral shaped cell, from a continuous roll. Recently, a flexible composite membrane cast from a random dispersion of ISE particles encapsulated into a polymer solution was used in conjunction with a conventional liquid electrolyte, thereby allowing for the use of ISE material with a flexible membrane and a wound cell. This membrane typically has too low of an ionic conductivity for electrochemical applications such as batteries, likely because of high interfacial resistance between the inorganic particles and polymer matrix.

Therefore, a need exists for an electrochemical membrane having an ISE that is both flexible and has high ionic conductivity.

SUMMARY

According to an embodiment, a solid state battery is provided with a flexible polymer sheet having a first side and a second opposed side. An array of ISE pillars is supported by a polymer matrix and the array extends through the sheet. Each of the pillars has an anode layer adjacent to the first side, a cathode layer adjacent to the second side, and an inorganic solid electrolyte (ISE) layer interposed between the anode and cathode layers.

According to another embodiment, a flexible electrochemical membrane is provided with a flexible polymer sheet having a first side and a second opposed side. An array of inorganic solid electrolyte pillars is supported by the polymer sheet. Each of the pillars having a first end adjacent to the first side and a second end adjacent to the second side such that each of the pillars extends through a thickness of the sheet and forms an ionically conductive pathway therethrough.

According to yet another embodiment, a method of forming an electrochemical membrane is provided. An inorganic solid electrolyte (ISE) precursor is deposited onto a substrate. The ISE precursor is patterned to form an array of solid state pillars containing an ISE material. A flexible polymer layer is deposited onto the substrate to surround and support each of the pillars. The substrate is removed to obtain a free standing membrane.

According to another embodiment, a method for forming an electrochemical membrane is provided. A first polymer layer is deposited onto a substrate. A second polymer layer is deposited onto the substrate. The first and second polymer layers are patterned to form a patterned surface. An inorganic solid electrolyte (ISE) material is deposited onto the patterned surface to form an array of solid state pillars containing the ISE material, with each of the pillars supported and surrounded by the first polymer layer. The second polymer layer is removed after the ISE material is deposited. The substrate is removed to obtain a free standing membrane.

Various embodiments of the present disclosure have many non-limiting advantages. For example, inorganic solid electrolytes are primarily used in applications such as thin film batteries having stacked layers and they require expensive vapor deposition techniques to produce them. Whereas, a free standing flexible composite solid electrolyte membrane described herein may be fabricated by combining cost effective techniques such as ceramic processing, etching, solution casting, and the like. The resulting composite membrane is flexible and therefore may be used across many technologies requiring a flexible electrochemical membrane or structures, such various solid state battery cell designs, including lithium ion batteries, fuel cell, flow cells, and the like. These membranes may dramatically improve performance of Li-ion batteries while eliminating or reducing the need for liquid electrolytes. Incorporation of vertically aligned ISE arrays into a polymer electrolyte matrix enhances the mechanical properties and ionic conductivity of the composite polymer films over existing polymer separator membranes. Enhancement in mechanical properties, such as hardness, provides suppression of lithium dendrite growth when used with lithium metal anodes. The ISE pillars provide a direct ionic pathway across the membrane, and a much higher ionic conductivity for the membrane.

BRIEF DESCRIPTION OF THE DRAWINGS

FIG. 3 is a cross sectional view of an electrochemical membrane according to another embodiment;

FIG. 4 is a cross sectional view of an electrochemical membrane according to yet another embodiment;

FIG. 6 is a cross sectional side view of a flexible solid state battery according to another embodiment;

FIG. 7 is a schematic illustrating a process for forming an electrochemical membrane according to an embodiment;

FIG. 8 is a schematic illustrating a process for forming a solid state battery according to an embodiment;

FIG. 9 is a schematic illustrating a process for forming an electrochemical membrane according to another embodiment;

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention. Description of constituents in chemical terms refers to the constituents at the time of addition to any combination specified in the description, and does not necessarily preclude chemical interactions among constituents of the mixture once mixed.

Figure 1:
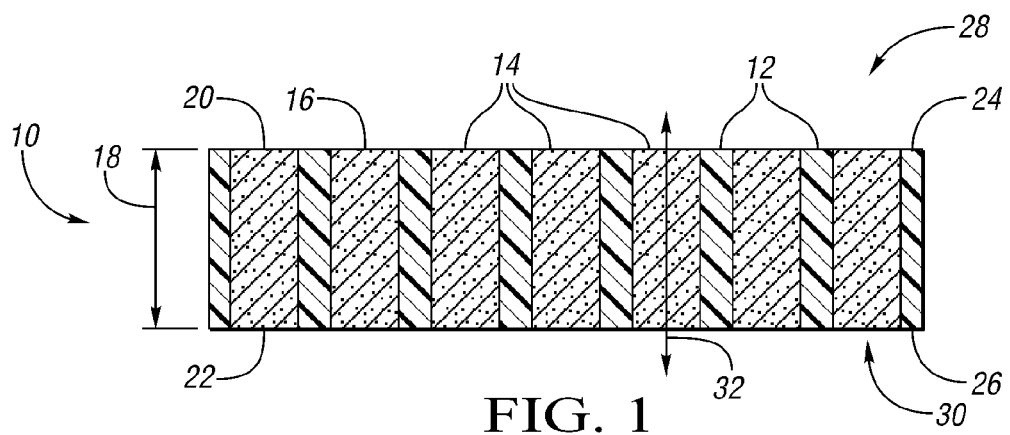
FIG. 1 is a cross sectional side view of an electrochemical membrane according to an embodiment.
Figure 2:
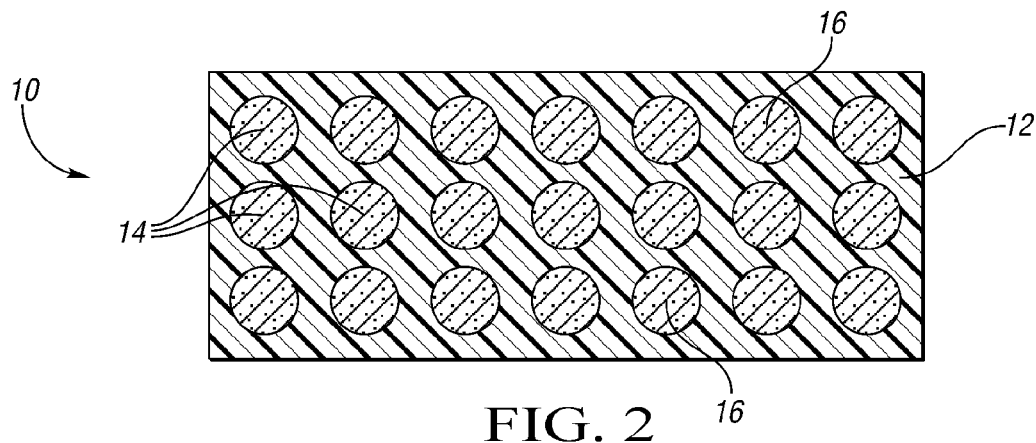
FIG. 2 is a top view of the membrane of FIG. 1.

FIGS. 1-2 illustrates a membrane 10 according to an embodiment of the present disclosure. The membrane 10 is free-standing and flexible. The membrane 10 is a composite of a polymer support or sheet 12 containing an array 14 of solid ISE pillars 16. The pillars 16 in the array 14 may be vertically aligned as shown. The pillars 16 of the array 14 may be joined together in the plane of the separator or membrane 10 using a polymer matrix provided by the polymer support 12.

The pillars 16 are continuous across the thickness 18 of the membrane 10. Each pillar 16 has a first end 20 and a second end 22 axially opposed to the first end. The first and second ends 20, 22 are exposed, and are not covered by the polymer sheet 12. The polymer sheet 12 has first and second sides 24, 26. The ends of the pillars 20, 22 may be co-planar with the first and second sides 24, 26 of the sheet, as shown in FIG. 1. In alternative embodiments, as described later with respect to FIGS. 3-4, one or both of the ends 20, 22 is not co-planar with the sides 24, 26 of the polymer sheet.

Each pillar 16 provides a direct, continuous ionically conductive pathway across the membrane 10 and through the polymer sheet 12 between a first side 28 of the membrane and a second side 30 of the membrane 10. This pathway is shown as arrow 32. The pillar 16, along with the pathway 32, may be aligned such that it is perpendicular to the plane of the membrane 10, as shown. In other embodiments, the pillar 16 and pathway 32 may be aligned at another angle with respect to the plane of the membrane 10. By providing pillars 16 extending across the membrane 10, the effect of interfacial resistance to ionic conduction between the inorganic particles through the polymer matrix is dramatically reduced as a pathway 32 is provided that does not cross an interfacial boundary.

The polymer 12 provides for flexibility within the membrane 10. The polymer 12 material permits the membrane 10 to be shaped in various manners, including a curved structure, a spiral, or another suitable shape for the application. The array 14 of ISE pillars 16 provides mechanical support for the membrane 10. Based on the application, the array 14 of ISE pillars 16 may also provide for mechanical suppression of dendrite growth compared to a conventional polymer-only porous membrane.

The ISE material for the pillars 16 is selected based on the application and chemical environment that the membrane 10 will be used with. The ISE material is selected such that it selectively permits transport of one or more ions, while providing a barrier to other ions or to diffusive transport across the membrane. The ISE material is typically selected to have a high ionic conductivity.

The polymer may be ionically conductive or ionically non-conductive, as desired for the application. Both the polymer material and the array material need to have a low electronic conductivity in order for use as an electrochemical separator or membrane.

The polymer may be provided as a single polymer, or as a blend of polymers or co-polymers. The polymer may include and support additional solid materials, such as fibers or particles to additionally provide for the desired material properties of the membrane. Alternatively, multiple polymer layouts may be provided. The polymer composition may be selected based on a number of factors, including, but not limited to, ionic conductivity, flexibility, bonding ability with the ISE material, mechanical strength, chemical compatibility, and the like.

The polymer 12 and ISE pillar 16 material in the array 14 provides for complete separation between the first and second sides 28, 30 of the membrane 10, such that only the selective transport of ions occurs through the ISE pillars 16 in the array 14 between the first and second sides 28, 30 of the membrane. If the polymer 12 material is ionically conductive, additional ion transfer may occur through the sheet 12. Therefore, different materials may be provided on each side of the membrane 10 without concern for mixing between the two, or mass transport across the membrane 10. An example of mass transport across a conventional membrane is oxygen or nitrogen transport across a proton exchange membrane in a fuel cell, leading to nitrogen and water accumulations on the fuel or anode side of the fuel cell stack, and the need to purge the fuel cell. By providing a membrane 10 in which hydrogen ions are selectively transported across the membrane and diffusive transport is limited or eliminated, fuel cell operation and efficiency is increased.

The array 14 may have variations in spacing between the pillars 16, and variations in arrangements and positioning of pillars 16. For example, the array may contain pillars 16 organized into rows and columns as shown in FIG. 1. Alternatively, the array 14 may contain pillars 16 that include offsets between rows or columns. The array 14 may also include variable spacing between the pillars, such that pillar density in one region is higher or lower than pillar density in another region.

Each pillar 16 is illustrated as being generally cylindrical. In other embodiments, the shape of the pillars 16 may vary and include rectangular prisms, polygonal prisms, elliptical prisms, and the like. The pillars 16 may also have a variable cross section along the axial length of the pillar 16, such as a frustoconical shape, such that the surface area at one end 20, 22 is different than the surface area at the opposed end 22, 20.

The membrane 10 as described may be used as a separator for a fuel cell, such as a proton exchange membrane (PEM) fuel cell, a direct methanol fuel cell (DMFC), a phosphoric acid fuel cell, or the like. The membrane 10 may be used with a flow cell, where the membrane acts as a separator between two circulating solutions or slurries. The membrane 10 may also be used in an ion exchange device where the flexible membrane is in a spiral structure and high surface areas are desirable, such as a water softener. The membrane 10 may also be used in gas separation process. The membrane 10 may be used in other applications, such as sensors including fluorine ion sensors.

FIGS. 3-4 illustrate other examples of flexible composite ISE membranes. The membrane 50 in FIG. 3 has the axial ends 52 of the pillars 54 flush or co-planar with the polymer support 56 on a first side 58 of the composite membrane 50. The other axial end 60 of the pillars 54 extends outwardly from the polymer support 56, such that an end region 62 of the pillars is exposed and the pillars 54 protrude from the support 56. This provides a larger surface area for the pillars 54 on that side 64 of the membrane. The increased surface area may then interface with more of the fluid or material on that side 64 of the membrane, which may allow for improved ionic transport.

The polymer support 56 has three layers of polymer that are co-planar with the membrane 50. A first and second polymer layer 66, 68 are exposed to the membrane environment. These polymers 66, 68 may be the same polymer material or different materials. A third polymer layer 70 is interposed between the first and second layers, and is made from a third polymer composition. In one example, the first and second (or outer) polymer layers 66, 68 are selected such that they are nonreactive or inert with the surrounding environment which may be different on opposed sides of the membrane 50. The middle third layer 70 is selected for a material property such as flexibility, or for other considerations such as cost or ease of manufacturing, since it is not directly exposed to the surrounding environment. The various polymer layers 66, 68, 70 may be the same thicknesses or vary in thickness. In alternative embodiments, any number of polymer layers may be used for the membrane 50.

FIG. 4 illustrates a membrane 80 with both axial ends 82, 84 of the pillars 86 extending outwardly from the polymer support 88, such that the end regions 90, 92 of the pillars are exposed and the pillars 86 protrude from the support 88 on both sides of the composite membrane. This provides a larger surface area for the pillars on both sides of the membrane.

Figure 5:
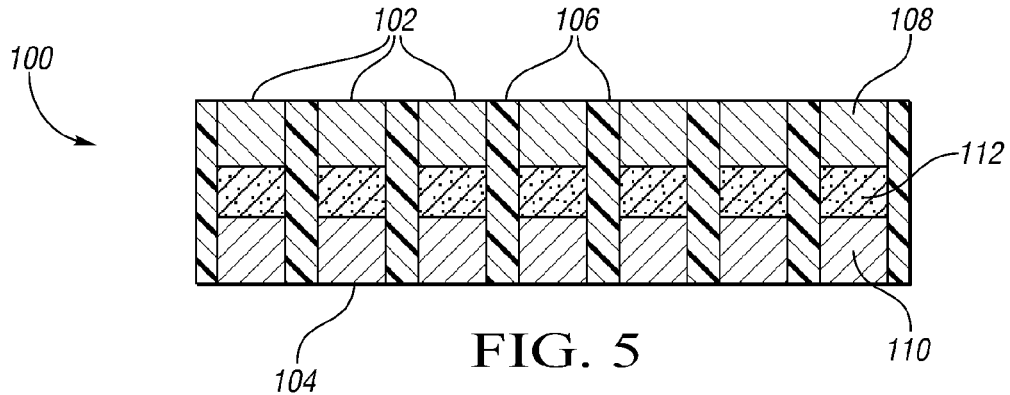
FIG. 5 is a cross sectional side view of a flexible solid state battery according to an embodiment.

FIG. 5 illustrates an embodiment of a flexible solid state battery 100 containing solid electrolytes. The battery 100 has an array 102 of solid state pillars 104 supported by a flexible polymer sheet 106. The polymer sheet 106 provides for a flexible battery structure that may be used, for example, in a jelly roll configuration. The solid state pillars 104 provide mechanical strength for the battery. The array 102 may be structured as described previously with respect to FIGS. 1-2.

In an embodiment, the solid state battery 100 is fabricated in a single flexible sheet as shown in FIG. 5. An array 102 of dense vertically aligned solid state pillars 104 is embedded in the polymer matrix 106. The solid state pillars 104 contain an anode layer 108, a cathode layer 110, and an inorganic solid electrolyte layer 112 interposed between the two 108, 110. Electrode layers 108, 110 may include active material and ISE material. The separator layer 112 contains only the ISE material. The ISE separator layer 112 material is selected based on the battery type such that it selectively transports only the desired ion, for example a lithium ion, while providing separation between the anode and cathode sides 108, 110. Therefore, there is no diffusive transport of other species across the ISE layer 112 or the polymer 106 to participate in side reactions, and the battery life may be extended.

During charging, lithium deintercalates from the cathode layer 110 and inserts into the anode. During discharging, lithium intercalates into the cathode 110. During the charging and discharging processes, lithium ions transport across the ISE electrolyte layer 112 to permit electrochemical energy storage or convert stored chemical energy into electrical energy.

Due to the separation between the anode and cathode sides 108, 110 due to the solid state nature of the battery and selective ionic transport through the ISE layer 112, different materials may be used on the anode side 108 and the cathode side 110 that may otherwise be incompatible.

In other embodiments, the ISE material and separator layer 112 used may be compatible with both non-aqueous and aqueous solvents. This composite membrane may then be used in batteries in conjunction with liquid electrolytes that are from either chemistry type, or in batteries that use both electrolyte types. In such a hybrid Li-ion battery design, the separator 112 provides complete isolation between the electrodes containing an aqueous electrolyte from the electrode containing a nonaqueous electrolyte and only permits selective ionic transfer across the membrane of the battery 100. This configuration may also reduce the overall amount of liquid organic electrolyte. The application of the solid state battery 100 described herein is not limited to Li-ion batteries, but may also be used in Li-air batteries or in other battery types and chemistries. For instance, the use of a composite membrane according to the present disclosure as a Li-air battery provides for ionic transport across the electrodes as well as inhibiting the permeation of oxygen to the lithium electrode. For solid conductors suitable for other ions ($Na^+$, $K^+$, $Mg^{++}$, $O_2^-$, etc.), the same design approach may be implemented as appropriate.

Additionally, in other embodiments, different fluids may be used on opposing sides of the separator that would otherwise be incompatible. For example, a lithium metal may be used on the anode side and air may be used as the cathode material. Alternatively, two different solutions may be used on the anode and cathode sides. In one embodiment, the anode and cathode layers 108, 110 in the solid state pillars may be provided with a degree of porosity such that the solutions flow through and interact with the anode and cathode materials, and aid in transport from the respective layer to the ISE layer. The cathode side solution and anode side solutions may be the same, or in alternative embodiments, may differ. For example, an aqueous solution may be used on one side and a non-aqueous solution on the other side of the battery. This may increase the battery performance, as direct contact between the anode or cathode layer and the ISE layer may be limited to physical boundaries between the two.

FIG. 6 illustrates another embodiment of a flexible composite solid state battery 120. The axial ends 122 of the ISE pillars 124 are flush or co-planar with the surface of the polymer support 126 on the anode side 128. The other axial end 130 of the ISE pillars 124 extends outwardly from the polymer support 126, such that an end region of the pillars is exposed and the pillars protrude from the support surface on the cathode side 132. The anode side of the polymer surface is provided with a thin film 134 of an anode material, such as lithium metal which is also flexible. The cathode side 132 of the ISE pillar 124 is left exposed to interact with a solution or fluid, such as air. The cathode side 132 of the pillars 124 has a larger surface area to interface with the air, which may allow for improved ionic transport. The polymer support 126 and solid ISE pillars 124 provides for selective ionic transport of the Li ion only, and prevents diffusive transport between the anode and cathode sides.

The batteries as described herein may be of various chemistries and architectures in the spirit and scope of the disclosure, and the examples described herein are intended to be non-limiting. The ISE material is selected such that the battery (or membrane) is selectively permeable for a desired ion. The battery may be a lithium battery, such as a lithium ion battery, lithium air battery, or the like. An ISE material may be selected that provides for single ion (lithium) conduction through the material. The ISE material may also be selected based on various material properties including, but not limited to, grain boundary resistance, ionic conductivity, electronic conductivity, stability against chemical reaction with electrode material, and thermal expansion coefficients compared to electrode material and/or polymer support material.

Lithium battery chemistries may include lithium ion batteries, lithium air batteries, lithium sulphur batteries, and the like. For a lithium battery, ISE materials may be selected from various lithium ion conductors, including materials selected from the following groups: (i) Na super ionic conductor (NASICON) structured lithium electrolytes, (ii) garnet type electrolytes, including those containing transition metals, (iii) perovskite type oxides, and (iv) glassy and glass ceramic electrolytes, including those based on nitrides, sulphides, borates, and phosphates. A NASICON structured lithium electrolyte may include $LiM_2(PO_4)_3$, where M=Ti, Zr, Ge, Hf. A garnet type electrolyte includes materials such as $Li_5La_3M_2O_2$, where M=Nb, Ta; or lithium lanthanum zirconia oxides (LLZO) such as $Li_7La_3Zr_2O_{12}$. A perovskite type electrolyte includes materials such as lithium lanthanum titanates. Glassy and glass ceramic electrolytes include materials such as sulfide glass ceramics including $Li_2S$ based oxysulfide glasses, and lithium superionic conductors (LISOCON) such as $Li_{14}Zn(GeO_4)_4$. Other lithium based ISE materials include lithium phosphorus oxynitrides (Li-PON), lithium aluminum titanium phosphates (LATP), lithium aluminum germanium phosphates (LAGP), and others as are known in the art.

Of course, the ISE material may be selected for selective ion transport in other metal ion batteries, such as for sodium ion batteries including NASICON or sulfonated tetrafluoroethylene based fluoropolymer-copolymer (NAFION), sodium air batteries, magnesium ion batteries, magnesium air batteries, and the like. The ISE materials listed herein are for example and are not intended to be limiting. One skilled in the art may select an appropriate ISE material based on the desired ionic transport and application.

One or more polymer materials may be selected for use with the battery (or membrane) that provide for stability against chemical reaction, flexibility, low electrical conductivity, and the like. The polymer sheet may include a single polymer, or may be a blend of multiple polymers or a co-polymer. In other embodiments, the polymer sheet includes layers of polymers, with different layers providing different desired characteristics for the polymer sheet. The polymer may also contain or support fibers or other solid material within the matrix.

The polymer material may include polyolefins such as polyethylene oxide (PEO), polypropylene oxide (PPO), or a polyethylene propropylene copolymer. Various polymers may be used as are known in the art, and include polymers with ether-based groups, such as PEO, PPO, and their copolymers, or others such as polyvinylidene fluoride (PVDF), polyacrylonitrile (PAN), and polymethyl-methacrylate (PMMA). The polymer material may be blended or crosslinked with compatible materials, such as polyacrylic acid (PAA), polymethylmethacrylate (PMMA), or polystyrene.

FIG. 7 illustrates a schematic of a process or method 150 for forming a flexible polymer composite electrochemical membrane according to an embodiment. FIG. 7 represents a non-limiting example of a wet process. In a first step 152 a substrate 154 is provided. An ISE precursor material 156 for synthesizing ISE is coated on to the substrate 154. The ISE precursor 156 may be coated onto the substrate using spin casting or another suitable technique such as chemical solution deposition including sol-gel for providing a thin, generally uniform coating of a liquid ISE precursor 156 onto the substrate.

The ISE precursor 156 is then patterned into a pillar array at 158. The patterning may be done using a mold 160, as shown in FIG. 7. The mold containing desired arrays 162 of ordered pores 164 is pressed onto the cast coating to create the array of ISE-precursor pillars replicating the pore structure of mold. Alternatively, the patterning may be done using a self-assembly technique, with the substrate being pre-coated with a material that causes the ISE precursor to self-pattern, separate, and form an array of pillars, for example, using a hydrophobic pre-coating. In other embodiments, the patterning is done using laser machining, embossing, mechanical milling, chemical etching, and the like after the precursor is cured into a solid form.

The ISE precursor is then cured into a solid form, for example, by heating or drying, and then the substrate and solid ISE precursor pillars are processed to obtain micro/macro pillars of fully functional ISE material at 166. The solid ISE precursor pillars may be processed using a number of techniques including, dense sintering, pressure assisted sintering, sintering with a flux material, and the like. The sintering process 166 causes densification of the material as well as grain growth, including refinement at grain boundaries. Sintering occurs by diffusion of atoms through the microstructure. The sintering process may also provide for chemical composition changes in the ISE precursor to provide the ISE material. The ISE material is now in an array 168 of pillars 170 on the substrate 154.

A polymer solution 172 is then coated onto the substrate to form a composite structure at 174. The polymer solution may be a single polymer, a polymer blend, a co-polymer, or one of several polymer layers. The polymer solution 172 may be deposited using spin casting, or another suitable technique including chemical solution deposition. The polymer flows onto the patterned surface and between the ISE material pillars 170 such that it surrounds each pillar 170. Finally, the composite film or structure is separated from the substrate by removing the substrate at 176. The substrate may be removed by etching, dissolution, peeling, or other suitable technique. The resulting membrane 178 may range between 1-500 microns in thickness, and in a further embodiment may be on the order of 25 microns in thickness.

FIG. 8 illustrates a process 200 or method for forming a flexible solid state battery according to a non-limiting example of a wet process. In a first step 202 a substrate 204 is provided. A cathode layer 206 containing the mixture of active material, carbon and ISE is formed as a film on the substrate, followed by a separator layer 208 containing ISE material or ISE precursor, and then followed by an anode layer 210 containing the mixture of active material and ISE. In alternative embodiments, the anode layer 210 may be cast on first, followed by the separator and cathode layers 208, 206. The cathode, separator, and anode layers 206, 208, 210 may each be coated using spin casting or another suitable technique such as chemical solution deposition including sol-gel for providing a thin, generally uniform coating. Each layer may be dried or cured before the next coating is applied.

This multilayer film 212 is patterned at 214 to create arrays 216 of vertical pillars 218 using any suitable patterning technique which may include laser machining, embossing, mechanical milling, chemical etching, and the like. The multilayer film 212 may be sintered to cause densification of the material as well as grain growth, including refinement at grain boundaries.

A polymer solution 217 is then coated onto the substrate to form a composite structure at 219. The polymer solution 217 may be a single polymer, a polymer blend, a co-polymer, or one of several polymer layers. The polymer solution 217 may be deposited using spin casting, or another suitable technique including chemical solution deposition. The polymer flows onto the patterned surface and between the pillars 218 such that it surrounds and supports each pillar 218. Finally, the composite film or structure 220 is separated from the substrate 204 by removing the substrate at 222. The substrate 204 may be removed by etching, dissolution, peeling, or other suitable technique. In one embodiment, cathode and anode layers 206, 210 may range from 25-200 microns in thickness, and the separator layer 208 may range between 1-50 microns in thickness.

FIG. 9 illustrates a process or method 250 for forming a flexible composite electrochemical membrane according to a non-limiting example of a dry process. In a first step 254 a substrate 252 is provided. A first polymer solution 256 is coated onto the substrate 252. A second polymer solution 258 is then coated onto the substrate 252. The polymer solutions 256, 258 may each be single polymer, polymer blends, a co-polymer, or the like. The polymer solutions 256, 258 may be deposited using spin casting, or another suitable technique such as chemical solution deposition including sol gel. The first polymer solution 256 may be dried before the second polymer layer 258 is applied. Additional polymer layers may also be coated onto the substrate to create other membrane or battery architectures, such as those shown in FIGS. 3-4.

The polymer layers 256, 258 are then patterned to create a patterned surface 260 at 262. For example, the patterned surface 260 provides a mold structure to later form the array of pillars of ISE material with the patterned surface 260 defining an array of recesses or apertures extending through the polymer layers. The patterning 262 may be done using laser machining, embossing, mechanical milling, chemical etching, lithography, and the like.

As a representative example, the two different polymer layers 256, 258 are coated onto a substrate 252 through casting of slurries or solutions, lamination or vapor deposition. The substrate 252 may be silicon or glass. As shown in FIG. 9, polymer-1 256 is used to form a polymer support layer film and polymer-2 258 (e.g. photoresist) is used as a sacrificial layer. After deposition, the polymer layers 256, 258 are patterned by embossing or through lithography.

An ISE material layer 264 is deposited onto to the substrate at 266, for example, using a dry process. The ISE material 264 may be deposited using sputtering, physical vapor deposition (PVD), chemical vapor deposition (CVD), pulsed laser deposition, or another suitable process. The ISE material 264 is deposited onto the substrate such that the ISE material fills in the array of recesses of the patterned surface 260, thereby forming an array 268 of ISE pillars 270 that are supported by the surrounding patterned polymer-1 layer 256.

The polymer-2 layer 258 is sacrificial and is removed at 272, for example, by dissolution with a suitable solvent. Finally, the composite film or structure 274 is separated from the substrate at 276 by removing the substrate. The substrate may be removed by etching, dissolution, peeling, or other suitable technique.

Of course, another membrane or composite electrochemical structure, such as those shown in FIGS. 3-4, may be provided using the dry process with additional polymer layers. Alternatively, the dry process may be used to provide a solid state battery as described herein by depositing a cathode layer followed by a separator layer and then an anode layer, or vice versa.

Presently, ISE are primarily used in applications such as thin film batteries having stacked layers and they require expensive vapor deposition techniques to produce them. A free standing flexible composite solid electrolyte membrane described herein may be fabricated by combining low cost techniques such as ceramic processing, etching, solution casting, and the like. The resulting composite membrane is flexible and therefore may be used across many technologies requiring a flexible electrochemical membrane or structure, such as various solid state battery cell designs, including lithium ion batteries, fuel cell separators, flow cells, and the like. These membranes may dramatically improve performance of Li-ion batteries while eliminating the need for liquid electrolytes. Incorporation of vertically aligned ISE arrays into a polymer electrolyte matrix enhances the mechanical properties and ionic conductivity of the composite polymer films over existing polymer separator membranes. Enhancement in mechanical properties, such as hardness, provides suppression of lithium dendrite growth when used with lithium metal anodes. The ISE pillars provide a direct ionic pathway across the membrane, and a much higher ionic conductivity for the membrane.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:
1. A flexible electrochemical membrane comprising:
a flexible polymer sheet having a first side and a second opposed side spaced apart by a thickness; and
an array of inorganic solid electrolyte pillars supported by the polymer sheet, each pillar extending through the thickness of the sheet with a first exposed end adjacent to the first side and a second exposed end adjacent to the second side to form an ionically conductive pathway across the sheet.

2. The membrane of claim 1 wherein the array of pillars is aligned with respect to a thickness of the membrane.

3. The membrane of claim 1 wherein each of the pillars is oriented generally perpendicular to a plane defined by the polymer sheet.

4. The membrane of claim 1 wherein the array of pillars provides mechanical strength for the membrane and wherein the polymer sheet interconnects the pillars to provide flexibility for the membrane such that one pillar is moveable relative to another pillar in the array.

5. The membrane of claim 1 wherein the polymer sheet has a first polymer layer formed from a first polymer in contact with a second polymer layer formed from a second polymer.

6. The membrane of claim 1 wherein the polymer sheet includes one of a co-polymer and a polymer blend.

7. The membrane of claim 1 wherein each of the pillars is generally cylindrical.

8. The membrane of claim 1 wherein at least one of the first and second exposed ends of each pillar is co-planar with the first and second sides, respectively, of the polymer sheet.

9. The membrane of claim 1 wherein at least one of the first and second ends of each pillar extends outwardly to protrude from the first and second sides, respectively, of the polymer sheet.

10. The membrane of claim 1 wherein each pillar has a variable cross section along an axial length of the pillar such that the first exposed end has a smaller surface area than the second exposed end of the pillar.

11. The membrane of claim 1 wherein the polymer sheet comprises a first layer providing the first side, a second layer providing the second side, and a third layer positioned between and connecting the first and second layers, the first and second layers selected to be inert with a surrounding environment.

12. A flexible electrochemical membrane comprising:
a flexible non-ionically conductive polymer sheet having a first side and a second opposed side; and
an array of inorganic solid electrolyte pillars, each pillar supported and surrounded by the polymer sheet, each pillar extending through a thickness of the sheet and having a first exposed end adjacent to the first side and a second exposed end adjacent to the second side to form an ionically conductive pathway therethrough.

13. The membrane of claim 12 wherein the first exposed end of each pillar protrudes from the first side of the polymer sheet.

14. The membrane of claim 12 wherein a length of each pillar between the first and second ends is at least the thickness of the sheet.

* * * * *